United States Patent
Yamazaki et al.

(10) Patent No.: US 6,937,339 B2
(45) Date of Patent: Aug. 30, 2005

(54) INSPECTION DEVICE AND SYSTEM FOR INSPECTING FOREIGN MATTERS IN A LIQUID FILLED TRANSPARENT CONTAINER

(75) Inventors: Hiromi Yamazaki, Hitachiota (JP); Tadahiro Katane, Hitachiota (JP); Hirohisa Fukuda, Hitachi (JP); Kunitaka Asano, Hitachi (JP); Mitsuhiro Matsushima, Matsudo (JP)

(73) Assignee: Hitachi Engineering Co., Ltd., Ibaraki (JP)

( * ) Notice: Subject to any disclaimer, the term of this patent is extended or adjusted under 35 U.S.C. 154(b) by 384 days.

(21) Appl. No.: 10/092,897

(22) Filed: Mar. 8, 2002

(65) Prior Publication Data

US 2002/0171054 A1 Nov. 21, 2002

(30) Foreign Application Priority Data

Mar. 14, 2001 (JP) ...................................... 2001-071642
Sep. 28, 2001 (JP) ...................................... 2001-301981

(51) Int. Cl.[7] .............................................. G01N 21/90
(52) U.S. Cl. .................................. 356/427; 356/239.6
(58) Field of Search ................................ 356/426, 427, 356/432, 433, 434, 435, 445, 448, 337–343, 239.4, 239.5, 239.6; 382/142

(56) References Cited

U.S. PATENT DOCUMENTS

| | | | |
|---|---|---|---|
| 3,942,897 A | 3/1976 | Takahashi et al. | |
| 4,335,960 A | 6/1982 | Ashcroft et al. | |
| 4,551,627 A | 11/1985 | Reich | |
| 4,664,525 A | * | 5/1987 | Tagaya ........................ 356/428 |
| 4,958,223 A | 9/1990 | Juvinall et al. | |
| 5,442,446 A | 8/1995 | Gerber et al. | |
| 5,443,164 A | 8/1995 | Walsh et al. | |
| 5,523,560 A | 6/1996 | Manique et al. | |
| 5,536,935 A | 7/1996 | Klotzsch et al. | |
| 6,064,479 A | 5/2000 | Knapp | |

FOREIGN PATENT DOCUMENTS

| | | | | |
|---|---|---|---|---|
| EP | 303175 A2 | 2/1989 | | |
| JP | 62-011944 | 1/1987 | | |
| JP | 63-282640 | 11/1988 | | |
| JP | 01-141342 | 6/1989 | | |
| JP | 7-92109 | 4/1995 | | |
| JP | 07-092109 | 4/1995 | | |
| JP | 407092108 A | * | 4/1995 | .......... G01N/21/84 |
| JP | 07-311160 | 11/1995 | | |
| JP | 8-136476 | 5/1996 | | |
| JP | 08-338815 | 12/1996 | | |
| WO | WO 90/13810 | 11/1990 | | |

* cited by examiner

Primary Examiner—Gregory J. Toatley, Jr.
Assistant Examiner—Roy M Punnoose
(74) Attorney, Agent, or Firm—Mattingly, Stanger, Malur & Brundidge, P.C.

(57) ABSTRACT

In an inspection device for inspecting for possible foreign matters contaminating a liquid filled transparent container, a red color illumination unit 23A is disposed behind a glass container 22 filled with liquid and a pair of blue color illumination units 23B and 23C are disposed so as to sandwich the red color illumination unit 23A. Both the red color and blue color illumination units 23A, 23B and 23C are disposed so that the red color light transmits through the glass container 22 and the blue color light reflected by a possible foreign matter in the liquid merges with the red color transmission light. Both the transmission light and the reflection light are separated by a color separation mirror 4 and are imaged by CCD cameras 5 and 6 so as to detect both black color series and white color series foreign matters can be detected at the same time.

3 Claims, 5 Drawing Sheets

TRANSMISSION LIGHT INSPECTION USE CAMERA PICTURE

FIG. 2(b)

REFLECTION LIGHT INSPECTION USE CAMERA PICTURE

# INSPECTION DEVICE AND SYSTEM FOR INSPECTING FOREIGN MATTERS IN A LIQUID FILLED TRANSPARENT CONTAINER

BACKGROUND OF THE INVENTION

1. Field of the Invention

The present invention relates to an inspection device and a system for inspecting foreign matters in liquid filled transparent containers.

2. Conventional Art

Liquids that fill transparent containers, for example, glass bottles and plastic containers, include those such as drinking water, soft drinks and medical related liquid such as those used for injections and nutrients. These transparent containers are subjected to an automatic inspection with regard to such parameters as shape and quality on a conveyer line, thereafter, liquid is filled into each of passed products, the volume of the filled liquid is automatically inspected and after pasting a label thereon, automatic inspection of the label pasting condition, or the like, is performed successively. Further, other than the above inspection, a foreign matter automatic inspection to determine whether or not foreign matters are contaminated into the liquid is performed. The foreign matters include a variety of things such as harmful ones, ones that are undesirable and ones which are acceptable and can be treated as food even if such foreign matters are technically contaminants.

Such foreign matters are frequently imaged by an imaging camera, are image processed in high speed and are detected through an automatic inspection.

There are many foreign matters of a black color series, but also there are foreign matters of a nebula color series. There are following facts that the foreign matters of the black color series can easily be imaged by making use of light transmission and the foreign matters of the nebula color series are easily be imaged by making use of light reflection.

However, it is unknown what sorts of foreign matters contaminate liquid, therefore, it is impossible to detect all sorts of foreign matters by making use of one of transmission light and reflection light, and there is a large demand for a foreign matter inspection machine which can detect all sorts of foreign matters.

Further, there is also a large demand for a foreign matter inspection machine which can specify the kinds of foreign matters contaminate the liquid.

SUMMARY OF THE INVENTION

An object of the present invention is to provide an inspection device and a system for inspecting foreign matters in liquid filled transparent containers which can detects a variety of foreign matters at substantially the time and can specified the detected foreign matters.

Another object of the present invention is to provide an inspection device for inspecting foreign matters in liquid filled transparent containers in which an arrangement structure of a transmission light source and a reflection light source thereof is simplified.

One of major aspects of an inspection device for detecting a foreign matter in a liquid filled transparent container according to the present invention is to provide an inspection use means on the opposite side of the transparent container at a position which permits observation from a same direction of both transmission light of first light from a first illumination light source transmitted through the transparent container and reflection light of second light from a second illumination light source which is caused by a possible reflective foreign matter contaminated in the liquid with respect to the transparent container, thereby, the possible foreign matter appears on a same position in both picture images formed from the transmission light and the reflection light.

An inspection device for detecting a foreign matter in liquid filled in a transparent container according to one aspect of the present invention comprises:

a first irradiation light source which is disposed behind the transparent container and irradiates a first irradiation light to the transparent container;

a second irradiation source which is disposed at a position other than behind the transparent container and irradiates a second irradiation light of a color other than that of the first irradiation light to the transparent container;

a color separation use mirror which is disposed on a transmission light optical path of the first irradiation light from the transparent container as well as on a reflection light optical path of the second irradiation light from the transparent container, which causes to advance in a straight optical path the transmission light of the first irradiation light and performs color separation of the reflection light of the second irradiation light and guides the same in another optical path than that of the transmission light;

a first imaging means which is disposed on the straight advancing optical path and images the transmission light of the first irradiation light;

a second imaging means which is disposed on the other optical path and images the reflection light of the second irradiation light; and an image processing means which image processes picture images taken by the first and second imaging means and detects foreign matters in the liquid filled container.

An inspection device for detecting a foreign matter in liquid filled in a transparent container according to another aspect of the present invention comprises:

a first irradiation light source which is disposed behind the transparent container and irradiates a first irradiation light to the transparent container;

a second irradiation source which is disposed at a position other than behind the transparent container and irradiates a second irradiation light of a color other than that of the first irradiation light to the transparent container;

a half mirror which is disposed on a transmission light optical path of the first irradiation light from the transparent container as well as on a reflection light optical path of the second irradiation light from the transparent container and performs optical path separation;

a first filter which is disposed on a straight advancing optical path of the half mirror and selects the transmission light from the first irradiation light;

a first imaging means which images the transmission light of the first irradiation light selected by the first filter;

a second filter which is disposed on another optical path of the half mirror and selects the reflection light of the second irradiation light;

a second imaging means which images the reflection light of the second irradiation light selected by the second filter; and an image processing means which image processes picture images taken by the first and second imaging means and detects foreign matters in the liquid filled in the container.

Further, in the inspection devices for detecting foreign matters in liquid filled in a transparent container according to the present invention as referred above, the image processing means detects foreign matters for every first and second picture images taken by the first and second imaging means as well as compares the foreign matters detected from the first and second picture images to judge characteristics of the foreign matters.

Still another aspect of the invention is to provide a foreign matter inspection system in which transparent contains that are filled with liquid are successively conveyed and the above referred to foreign matter inspection device is disposed along the conveying route.

A further aspect of the present invention is to provide an inspection device for inspecting foreign matters in the liquid filled transparent container which comprises;

a first irradiation light source which is disposed behind the transparent container and irradiates a first irradiation light to the transparent container;

a second irradiation light source which is disposed adjacent the first irradiation light source and irradiates a second irradiation light to the transparent container from a direction different from that of the first irradiation light;

an imaging means which image takes transmission light on a transmission light optical path of the first irradiation light from the transparent container as well as image takes irregular reflection light of the second irradiation light; and a detection means which detects foreign matters in the liquid filled in the transparent container based on the picture images taken by the imaging means.

A still further aspect of the present invention is to provide a foreign matter inspection device for inspecting foreign matters in a liquid filled transparent container which comprises:

a first irradiation light source which is disposed behind the transparent container and irradiates a first irradiation light to the transparent container;

a second irradiation light source which is disposed adjacent to the first irradiation light source and irradiates a second irradiation light of a different color from that of the first irradiation light from different direction from that of the first irradiation light to the transparent container;

a color separation use mirror which is disposed on a transmission light optical path of the first irradiation light from the transparent container as well as on a reflection light optical path of the second irradiation light from the transparent container, which causes to advance in a straight optical path the transmission light of the first irradiation light and performs color separation of the reflection light of the second irradiation light and guides the same in another optical path than that of the transmission light;

a first imaging means which is disposed on the straight advancing optical path and images the transmission light of the first irradiation light;

a second imaging means which is disposed on the other optical path and images the reflection light of the second irradiation light; and an image processing means which image processes picture images taken by the first and second imaging means and detects foreign matters in the liquid filled container.

A still further aspect of the present invention is to provide a foreign matter inspection device for inspecting foreign matters in liquid filled in a transparent container which comprises:

a first irradiation light source which is disposed behind the transparent container and irradiates a first irradiation light to the transparent container;

a second irradiation light source which is disposed adjacent to the first irradiation light source and irradiates a second irradiation light of a different color from that of the first irradiation light from a different direction from that of the first irradiation light to the transparent container;

a half mirror which is disposed on a transmission light optical path of the first irradiation light from the transparent container as well as on a reflection light optical path of the second irradiation light from the transparent container and performs optical path separation;

a first filter which is disposed on a straight advancing optical path of the half mirror and selects the transmission light from the first irradiation light;

a first imaging means which images the transmission light of the first irradiation light selected by the first filter;

a second filter which is disposed on another optical path of the half mirror and selects the reflection light of the second irradiation light;

a second imaging means which images the reflection light of the second irradiation light selected by the second filter; and an image processing means which image processes picture images taken by the first and second imaging means and detects foreign matters in the liquid filled in the container.

DETAILED DESCRIPTION OF PREFERRED EMBODIMENTS

Figure 1:
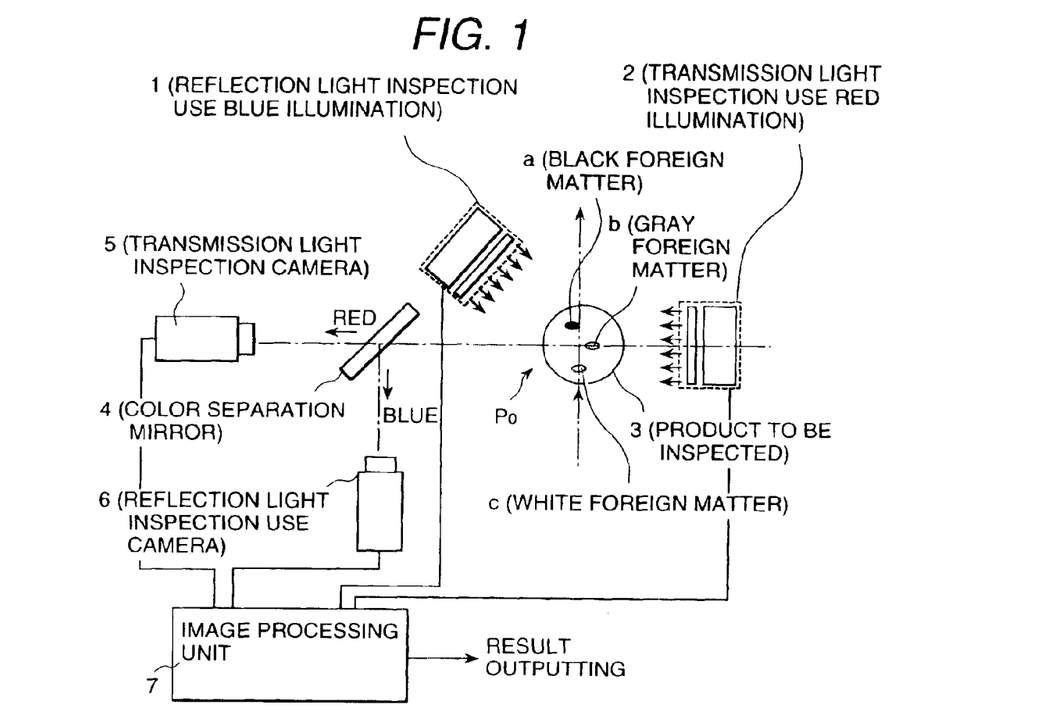
FIG. 1 is a diagram showing a foreign matter inspection device for inspecting foreign matters in a liquid filled transparent container representing a first embodiment according to the present invention.

FIG. 1 is a diagram showing a first embodiment of a foreign matter inspection device according to the present invention. Such foreign matter inspection device is disposed, for example, along a sanitation controlled conveyer line in which glass containers such as ampuls and vials are successively conveyed, and performs foreign matter inspection successively in high speed. The foreign matter inspection device is to detect at the same time white color foreign matters representing nebula color series foreign matters contained in liquid filled glass container 3 and black color foreign matters representing black color series foreign matters. The foreign matter inspection device has a blue color illumination unit 1 which is disposed at a diagonal with respect to the front side of the glass container 3, a red color illumination unit 2 disposed behind the glass container 3, a CCD camera 5 used for detecting transmission light, a color separation mirror (dichroic mirror performing separation depending on wavelengths) 4 which is disposed on an optical path line connecting the CCD camera 5, the glass container 3 and the red color illumination unit 2 and between the CCD camera 5 and the glass container 3, another CCD camera 6 used for inspecting reflection light which receives a color separated by the color separation mirror 4 and an image processing unit 7. Both CCD cameras 5 and 6 are cameras which perform monochromatic multi-gradation imaging.

In order to align the reflection light optical path of the irradiation light source 1 with the transmission light optical path of the irradiation light source 2, the positions of the irradiation light sources 1 and 2 are adjusted and such that both optical paths are aligned on a same line on which the color separation mirror 4 is disposed.

In the present embodiment, the illumination unit 2 is disposed behind the glass container 3 and irradiates red color light to the glass container 3, of which transmission light is imaged by the CCD camera 5. The blue illumination unit 1 is disposed at the diagonal front side of the glass container 3 and irradiates blue color light to the glass container 3, of which reflection light is imaged by the CCD camera 6. Both illumination units 1 and 2 are, for example, a halogen stroboscope or a laser beam source. The color separation use mirror 4 is a separation filter which transfers the red color light representing the transmission light to the CCD camera 5 and transfers the blue color light representing the reflection right to the CCD camera 6.

Since the red color illumination unit 2 and the blue color illumination unit 1 perform irradiation at the same time, and red and blue colors are separated at the color separation mirror 4, picture images of foreign matters on both the reflection light optical path and the transmission light optical path can be imaged at the same time.

The imaging plane of the CCD cameras 5 and 6 extend to cover the entire area of the liquid filled in the glass container 3, and, likely, the blue color illumination unit 1 and the red color illumination unit 2 also generate illumination light which covers the entire liquid filled in the glass container 3 by one time illumination.

The image processing unit 7 performs illumination control which turns ON the blue color illumination unit 1 and the red color illumination unit 2 at the time of inspection, and turns OFF the same at the time of non-inspection period, as well as controls the intensity of the respective illumination lights. Further, the image processing unit 7 takes in the picture images taken by the CCD cameras 5 and 6 performs image processing for the respective picture images taken in and detects foreign matters imaged by transmission light as well as imaged by the reflection light. Still further, since picture images of two sorts taken from the same direction and at the same moment can be obtained which permits comparison therebetween, the image processing unit can perform judgment of the characteristics of the foreign matters by comparing the foreign matters detected from the respective picture images.

Now, operation of FIG. 1 embodiment will be explained.

The glass containers 3 successively arrive at a foreign matter inspection position $P_o$ as shown in FIG. 1 through a conveyer line as indicated by an arrowed dashed line and are treated as a foreign matter inspection object. Although, it is possible to perform the inspection once by stopping the respective glass containers 3, however, since a high speed imaging is performed, an automatic inspection can be performed while continuously conveying the glass containers 3.

Now, when a glass container 3 arrives at the inspection position $P_o$, the arrival of the glass container 3 is detected by a proximity sensor (not shown) and a signal representing the arrival is sent to the image processing unit 7. The image processing unit 7 immediately turns ON the blue color and red color illumination units 1 and 2 at the same time and commands to turn ON the CCD camera 5 and 6 and start the imaging operation thereby. The flat shaped red color light from the red color illumination unit 2 passes the glass container 3, the transmission light is imaged by the CCD camera 5 after being sent and received by the CCD camera 5 via the color separation mirror 4. Likely, the blue reflection light is imaged by the CCD camera 6 after being sent and received by the CCD camera 6 via the color separation mirror 4.

Figures 2A, 2B:
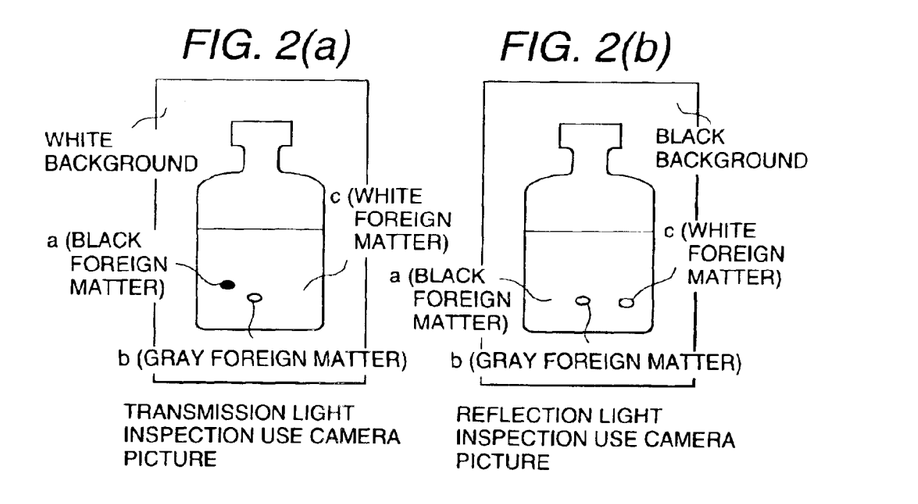
FIGS. 2(a) and 2(b) are examples of picture images of foreign matters taken by the first embodiment.

FIGS. 2(a) and 2(b) show examples of picture images taken by the FIG. 1 embodiment device. FIG. 2(a) shows a picture image example taken by the CCD camera 5, and FIG. 2(b) shows a picture image example taken by the CCD camera 6. Further, although the background color of FIG. 2(a) is white, and the background color of FIG. 2(b) is actually black, however, in view of visibility of the drawing the white color background is used for FIG. 2(b). According to FIG. 2(a) under white color background a picture image of a black color foreign matter "a" and a gray color foreign matter "b" were taken, but a picture image of a white color foreign matter "c" was not taken. On the other hand, according to FIG. 2(b) under black color background a picture image of the gray color foreign matter "b" and the white color foreign matter "c" were taken but a picture image of the black color foreign matter "a" was not taken.

Now, the black color foreign matter "a" and the white color foreign matter "c" will be explained. Examples of the black color foreign matter "a" are powders of such as a metal die and a process machine used at the time of molding the glass containers. On the other hand, examples of the white color foreign matter "c" are such as glass and solid component which is an effective component in the liquid but has not been sufficiently dissolved in the liquid. The gray color foreign matter "b" is a foreign matter of an intermediate color between black color foreign matter "a" and the white color foreign matter "c". It is predetermined which foreign matters (including harmful ones) among the foreign matters "a", "b" and "c" should be excluded. For example, such condition is preset that black color foreign matters should be excluded, white color foreign matters should not be excluded and intermediate color foreign matters should be excluded by treating the same as the black color foreign matters. The exclusion is performed for every glass container, and the concerned glass container itself is selected as a defective product and is excluded from the line and removed.

The image processing unit 7 takes in the picture images of the CCD cameras 5 and 6 as shown in FIGS. 2(a) and 2(b). With regard to examples in FIGS. 2(a) and 2(b), with the picture image in FIG. 2(a) the black color foreign matter "a" and the gray color foreign matter "b" can be detected, but the white color foreign matter "c" can not be detected, on the other hand, with the picture image in FIG. 2(b) the gray color foreign matter "b" and the white color foreign matter "c" can be detected, but the black color foreign matter "a" can not be detected.

Herein, the detection of the respective foreign matters "a", "b" and "c" is determined, for example, depending on the magnitude of pixel density (pixel value). In connection with FIG. 2(a) detection use threshold values TH1 and TH2 are respectively predetermined for a black color foreign matter "a" and for a gray color foreign matter "b", wherein TH1>TH2 and in connection with FIG. 2(b) detection use threshold values TH3 and TH4 are respectively predetermined for a gray color foreign matter "b" and a white color foreign matter "c", wherein TH3>TH4, and when assuming that a pixel value at a certain position (i, j) is dij and if $dij^2 TH1$, a foreign matter at the position (i, j) is judged as a black color foreign matter;

if $TH1 > dij^3 Th2$, a foreign matter at the position (i, j) is judged a gray color foreign matter;

if $dij^2 TH4$, a foreign matter at the position (i, j) is judged as a white color foreign matter; and if $TH4 < dij^2 Th3$, a foreign matter at the position (i, j) is judged as a gray foreign matter.

The values of i, j cover all of the pixel positions. Other than the above first judgment method using the threshold values, when a second judgment logic which will be explained below is used together, characteristics (such as black color, white color and gray color) of the foreign matters can be automatically judged to thereby enhance detection accuracy. Namely, when a common foreign matter is detected in both picture images of the CCD cameras 5 and 6 the foreign matter is possibly a gray color foreign matter "b", when a foreign matter is detected only in a picture image of the CCD camera 5, the foreign matter is possibly a black color foreign matter "a" and when a foreign matter is detected only in a picture image of the CCD camera 6, the foreign matter is possibly a white color foreign matter "c". Therefore, if the judgments of the both methods match each other, the matters can be specified absolutely foreign matters and if the judgments do not match each other, it is predetermined to perform judgment according to priority of the judgment methods. If such foreign matter can be specified, the region where the concerned foreign matter exists is coded binary, labeled and attaches a name of foreign matter which are used as management data later.

Further, in the picture images of FIGS. 2(a) and 2(b) it is designed that the foreign matters "a", "b" and "c" appear at the same positions and with substantially the same sizes, for this purpose, it is a precondition that the positions of the illumination units 1 and 2 and the CCD cameras 5 and 6 are set as designed.

Figure 3:
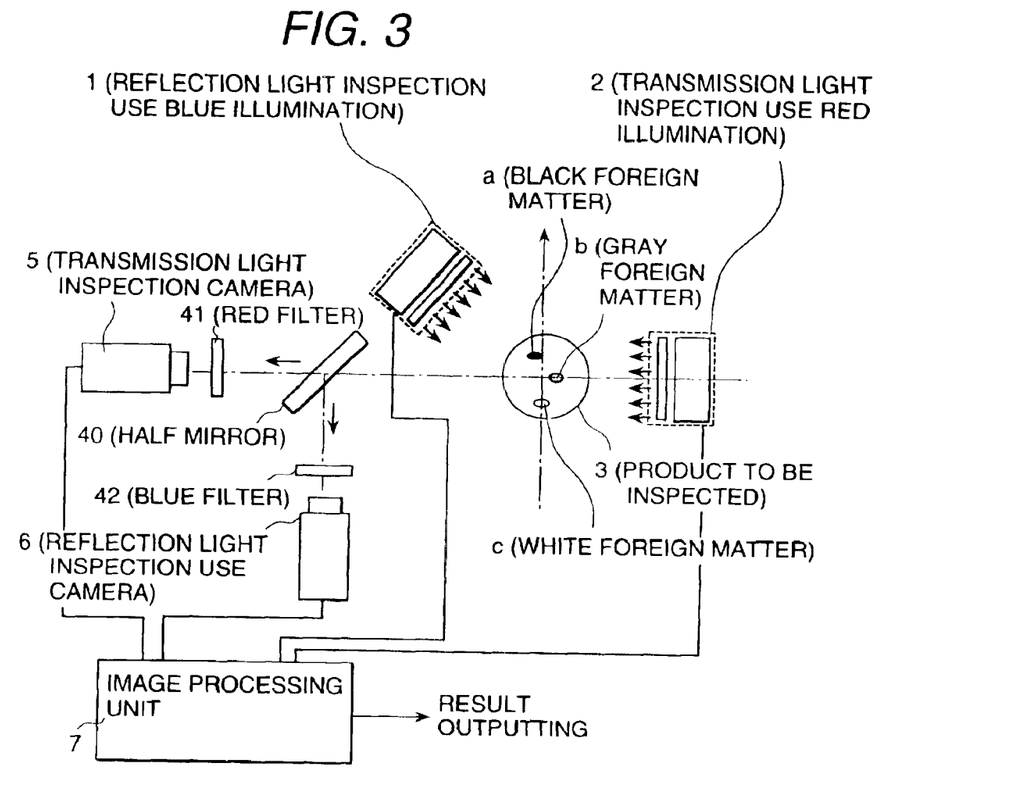
FIG. 3 is a diagram showing a foreign matter inspection device for inspecting foreign matters in a liquid filled transparent container representing a second embodiment according to the present invention.

FIG. 3 is a diagram showing a second embodiment of the present invention, in the present inspection device, in place of the color separation mirror 4 a half mirror is disposed at the position of the color separation mirror 4, at a position immediately before light incidence to the CCD camera 5 a red color filter 41 is provided and at a position immediately before light incidence to the CCD camera 6 a blue color filter 42 is provided. The half mirror 40 divides the incidence light into two portions, the red color filter 41 only passes red color light and the blue color filter 42 only passes blue color light.

A manner of foreign matter detection with the thus constituted FIG. 3 embodiment is substantially the same as that of FIG. 1 embodiment.

In the above first and second embodiment, the blue color is used for the reflection light and the red color is used for the transmission light, however, other than the above, many combinations, for example, as follows can be used.

| Reflection Light | Transmission Light |
| --- | --- |
| Red | Blue |
| Green | Red |
| Red | Green |

With regard to color combination, if the colors are different and the colors can be separable, any color combinations can be used. Further, the present embodiments are explained with reference to a still liquid in a container, the present embodiment are applicable to a foreign matter inspection in which liquid is caused to be rotated in the container. Further, the present embodiments are applicable to other transparent containers other than glass containers, such as plastic containers. Although it is preferable that the inner liquid is transparent, however, the present embodiments can also be applicable to somewhat opaque liquid. According to the first and second embodiments, by making use of the transmission light and the reflecting light each having different colors, a possible foreign matter in the liquid filled in the transparent container can be detected at the same time and further, the characteristics of the detected foreign matter can be specified.

Figure 4:
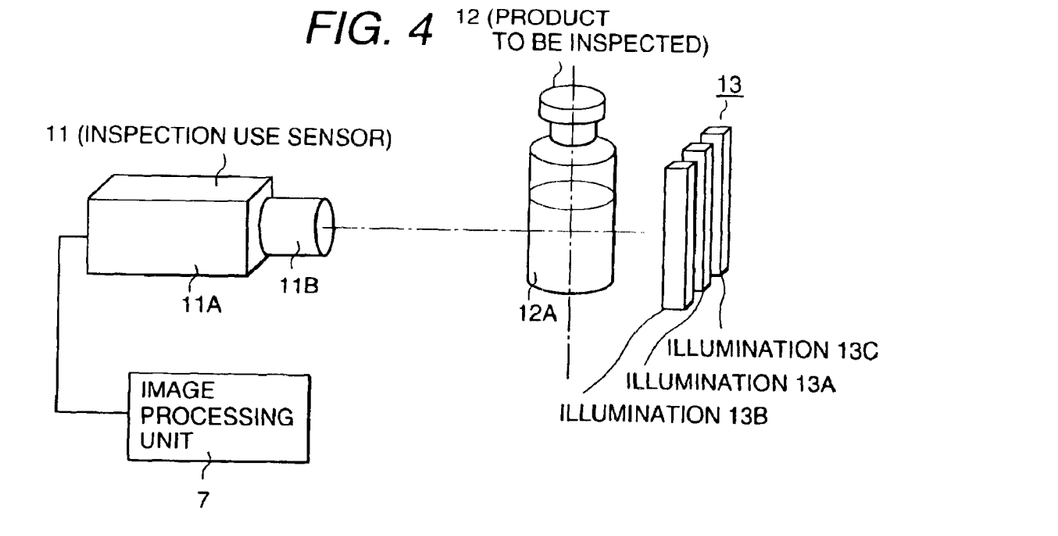
FIG. 4 is a diagram showing a foreign matter inspection device for inspecting foreign matters in a liquid filled transparent container representing a third embodiment according to the present invention.

FIG. 4 is a diagram showing a third embodiment of a foreign matter inspection device according to the present invention. The foreign matter inspection device for automatically inspecting foreign matters in liquid 12A filled in products 12 be inspected which are successively passed on a conveyer line and is constituted by an inspection use sensor 11, an illustration 13 and an image processing unit 7. The products 12 to be inspected is a cylindrical transparent container filled with liquid such as nutrient liquid, injections and soft drinks, more specifically, ampuls, vials and plastic bottles. Foreign matters in the liquid 12A includes process powder caused during processing the containers and powders contaminated into the liquid during the manufacture of the liquid and shows a variety of colors from black to white.

The inspection use sensor 11 is constituted by, for example, a CCD camera unit 11A and an image forming lens unit 11B thereof. The illumination 13 is constituted by a first illumination 13A and second illuminations 13B and 13C having a same color. The illumination 13 is configured to form a line shaped light source which covers an entire longitudinal length of the cylindrical container as its irradiation field. The first illumination 13A positions so as to oppose to the lens image taking face of the CCD camera portion 11A while placing the products 12 to be inspected therebetween as well as is disposed at the position of a focal distance of the transparent cylindrical container 12 serving as a lens. Thereby, a first light from the first illumination 13A transmits through the product 12 to be inspected and makes incidence into the image taking face of the CCD camera 11A as it is. The second illuminations 13B and 13C are disposed at positions which do not oppose to the lens image taking face but is disposed at the position of a focal distance of the container serving as a lens. Accordingly, second lights from the second illuminations 13B and 13C transmit through the products 12 to be inspected and advances in the direction other than the lens image taking face. As an alternative one of the two second illuminations can be used. Hereinbelow, an example when only one second illumination is activated will be explained.

Although, the first light is incident into the imaging plane, however, if there is a foreign matter in the liquid, the silhouette or shadow of the foreign matter also is incident as it is. On the other hand, the transmission light of the second light is not incident into the imaging plane, therefore, the silhouette of the foreign matter likely is not incident. However, the second light causes irregular reflection at the foreign matter and only the irregular reflection light thereof is incident into the imaging plane. Therefore, in the present embodiment at a certain timing the first illumination 13A is turned ON and the transmission light is imaged through the lens portion 11B and at another timing the second illuminations 13B and 13C are turned ON and the irregular reflection light is imaged through the lens portion 11B. The respective picture images that are taken are received by the image processing unit 7 and are processed separately therein to inspect foreign matters. The inspection includes such as existence and absence of foreign matters, size of foreign matters and kinds of foreign matters which are respectively realized according to variety of foreign matter detection programs prepared in advance. As has been explained above in the present embodiment by making use of a single inspection use sensor 11 and turning ON the first illumination 13A and the second illumination 13B at different timings, separate picture images of transmission light and of irregular reflection light are obtained which are likely processed separately.

In the above embodiment, the same color is exemplified for the first illumination 13A and the second illumination 13B, however, as an alternative or modification different colors can be used. For example, red color light is used for the first illumination 13A and blue color light is used for the second illumination 13B (as well as 13C). In this instance, when a single inspection use sensor 11 can still be used, if a color camera is used therefor, the picture image can be taken at the same time not at the different timing because the color components in the picture image can be separated afterward to obtain two separate picture images.

Figures 5A, 5B, 5C, 6A:
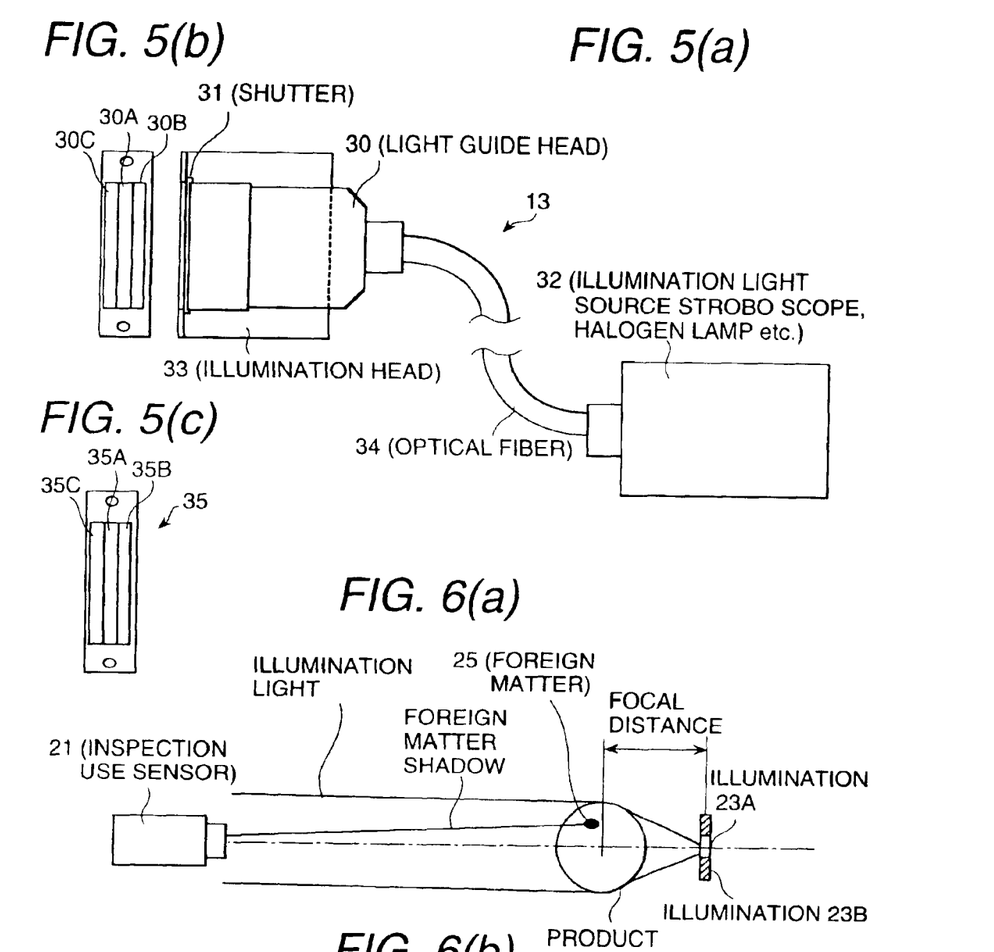
FIG. 5(a) is an outlook of a light guide device used in the third embodiment.
FIG. 5(b) is a front view of FIG. 5(a) and FIG. 5(c) is a modification of FIG. 5(b).
FIG. 6(a) is a view for explaining how picture images of foreign matters are taken by transmission light according to the FIG. 4 embodiment.

FIG. 5(a) shows a specific example of the illumination 13. For the illumination 13 a device called as a light guide is used. The light guide is one which is easy to handle and draw around the light from a light source by making use of an optical fiber and to bring the light freely to an inspection site so as to utilize the same as illumination. Such illumination 13 is constituted by a light guide head 30, an illumination light source 32, an illumination head 33 and an optical fiber 34. The illumination light source 32 is a light source such as a stroboscope, a halogen light and a laser, and the generated light thereby is guided by the optical fiber 34 up to the light guide head 30. The light guide head 30 is supported and secured by the illumination head 33. At the front face of the illumination head 33 an optical shutter 31 is provided.

The front face of the light guide portion 30 is provided with three vertical line shaped light emitting faces 30A, 30B and 30C. The light emitting face 30A corresponds to the first illumination 13A in FIG. 4 and the light emitting faces 30B and 30C respectively correspond to the second illuminations 13B and 13C. With this light guide respective vertical line shaped lights are emitted respectively from the light emitting faces 30A, 30B and 30C.

The optical shutter 31 is used for selecting emitting lights from the light emitting faces 30A, 30B and 30C. When the light emitting face 30A is selected, the face thereof in the light advancing direction is opened, and when the light emitting face 30B or 30C is selected the faces thereof in the light advancing direction are controlled to be opened. The shutter change-over can be performed either by mechanically or by electrically.

As an alternative of FIGS. 5(a) and 5(b) illumination 13, in place of the shutter 31, a colored filter 35 can be used as shown in FIG. 5(c). Three colored filters 35A, 35B and 35C are provided in place of the shutter 31 so as to correspond to the liner shaped light emitting faces 30A, 30B and 30C. The colored filter 35A is, for example, red color and the colored filters 35B and 35C are blue color. Accordingly, the light from the linear shaped light emitting face 30A represents red color light after passing through the colored filter 35A and lights from the linear shaped light emitting faces 30B and 30C represent blue color light after passing through the colored filters 35B and 35C.

When the red color light and the blue color light are emitted at the same time, the selective use of the colored filters 35A, 35B and 35c is unnecessitated.

Figure 6B:
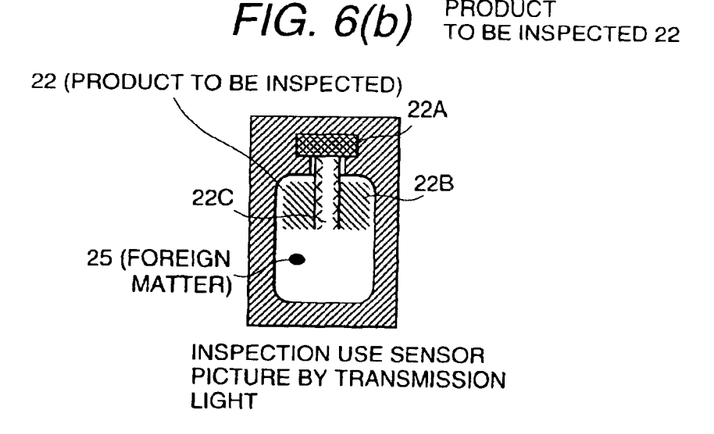
FIG. 6(b) is an example of picture imaged with the transmission light by FIG. 4 embodiment.
Figures 7A, 7B:
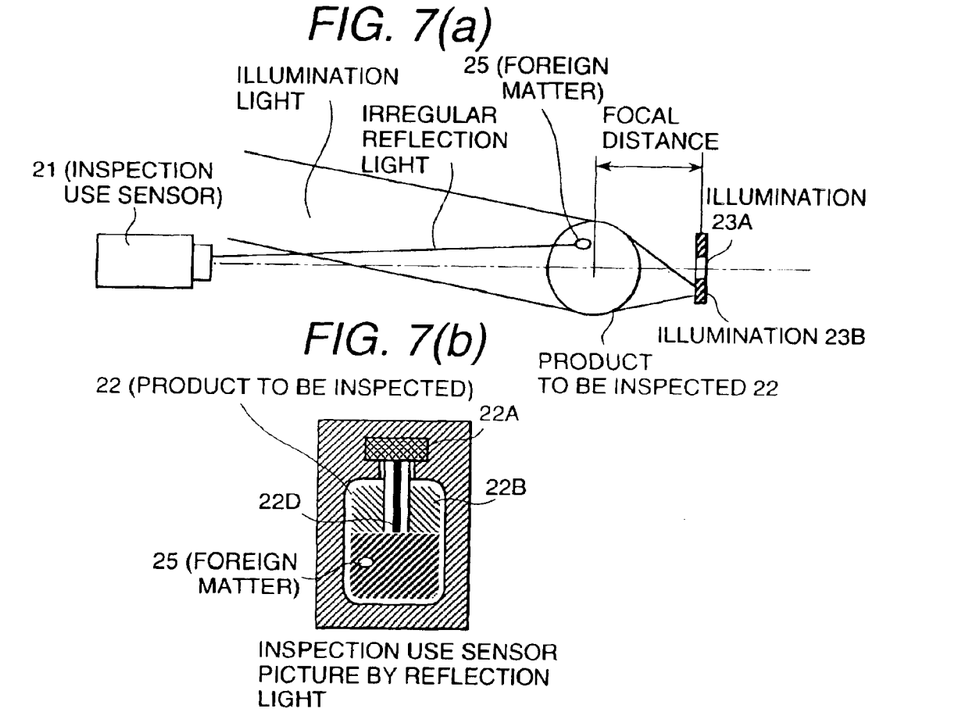
FIG. 7(a) is a view for explaining how picture images of foreign matters are taken by irregular reflection light according to the FIG. 4 embodiment.
FIG. 7(b) is an example of picture imaged with the reflection light by FIG. 4 embodiment.

The foreign matter imaging operation will be explained with reference to FIGS. 6(a), 6(b) and 7(a) and 7(c). FIGS. 6(a) and 6(b) show an example when a transmission light is imaged and FIGS. 7(a) and 7(b) show an example when a reflection light is imaged. In FIGS. 6(a) through 7(b), the illumination 23 is disposed at a focal position of the cylindrical container 22, in that the product to be inspected exhibiting a lens effect. The lens effect implies a phenomenon in which when parallel light beams are irradiated onto the cylindrical container 22, the cylindrical container 22 acts as if it were a lens and the parallel beams are focused. The illumination 23 is disposed at such focal position of the cylindrical container 22.

The emitted light from the illumination 23A in FIG. 6(a) passes along an optical path indicated arrows and is directed to the inspection use sensor 21. When there is a foreign matter 25 in the liquid filled in the product 22 to be inspected and the foreign matter 25 is a black color or nonlight transmission foreign matter, the foreign matter appears as a silhouette and focuses as a black color picture image which is shown in FIG. 6(b). In FIG. 6(b), 22A is a cap of the container 22, 22B is a space in the container 22 where no liquid is filled. Further, 22C is a picture image of the linear shaped light emitting face 23A.

FIG. 7(a) shows an example in which the illumination 23B is used as a light source. Since the illumination 23B is disposed in such a manner that the parallel beams therefrom do not direct to the inspection use sensor 21, the transmission light is directed as shown in FIG. 7(a). When there is, for example, a white color foreign matter 25 of reflection property in the liquid, the light is caused irregular reflection at this foreign matter 25, and the irregular reflection light directed to the inspection use sensor 21 is imaged by the sensor 21. FIG. 7(b) shows the picture imaged, and 25 is a picture image of the foreign matter, 22B is a space in the container 22 where no liquid is filled and while lines 22D are picture images of linear shaped light emitting faces of the illuminations 23B and 23C.

Figure 8:
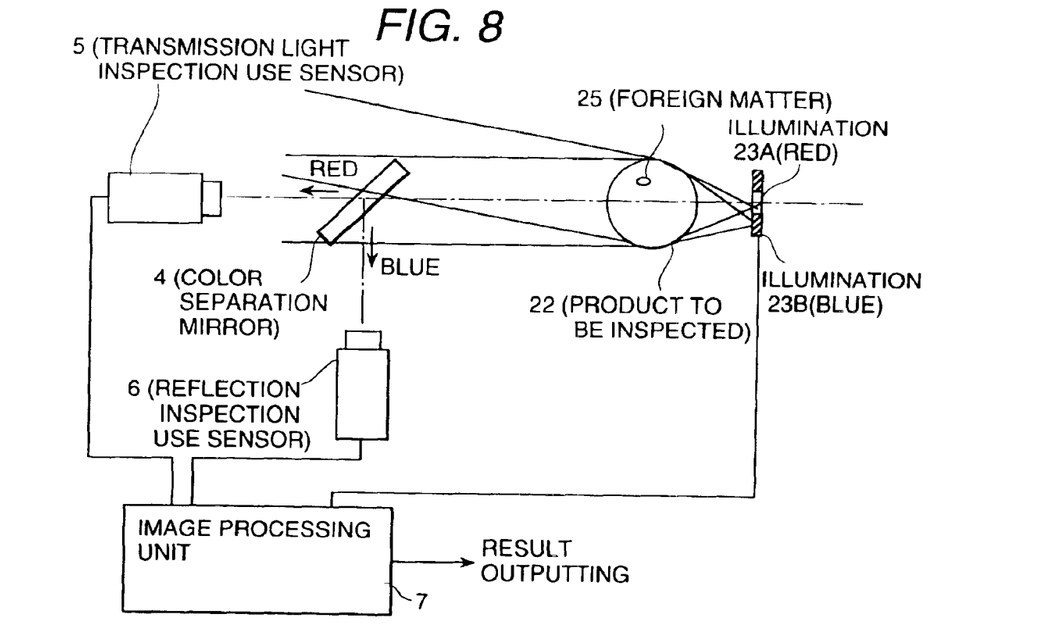
FIG. 8 is a diagram showing a foreign matter inspection device for inspecting foreign matters in a liquid filled transparent container representing a fourth embodiment according to the present invention.

FIG. 8 is a fourth embodiment of the present invention and a modification of FIG. 1 embodiment in which through the use of the color separation mirror 4 the lights for transmission and for reflection are emitted at the same time from the illumination 23A and the illuminations 23B and/or 23C. In the present embodiment, the foreign matter inspection device includes two inspection sensors 5 and 6 and the color separation mirror 4, and the red color illumination 23A and the blue color illumination 23B are turned ON at the same time. The color separation mirror 4 passes the separated red color light to the inspection sensor 5 and the separated blue color light to the inspection sensor 6.

With such arrangement, when the illuminations 23A and 23B are turned ON at the same time, the red color light is incident into the inspection use sensor 5 and the blue color light is incident into the inspection use sensor 6, and if there is a black color foreign matter 25 in the liquid, the silhouette thereof is imaged at the inspection use sensor 5 and if there is a white color foreign matter in the liquid, the reflection figure thereof is imaged at the inspection use sensor 6. In this instance, it seems that the reflective foreign matter image is also is incident into the inspection use sensor 5, however, the transmission of the blue color light is prevented by the color separation mirror 4 and the incidence and imaging thereof at the inspection use sensor 4 are prevented.

Figure 9:
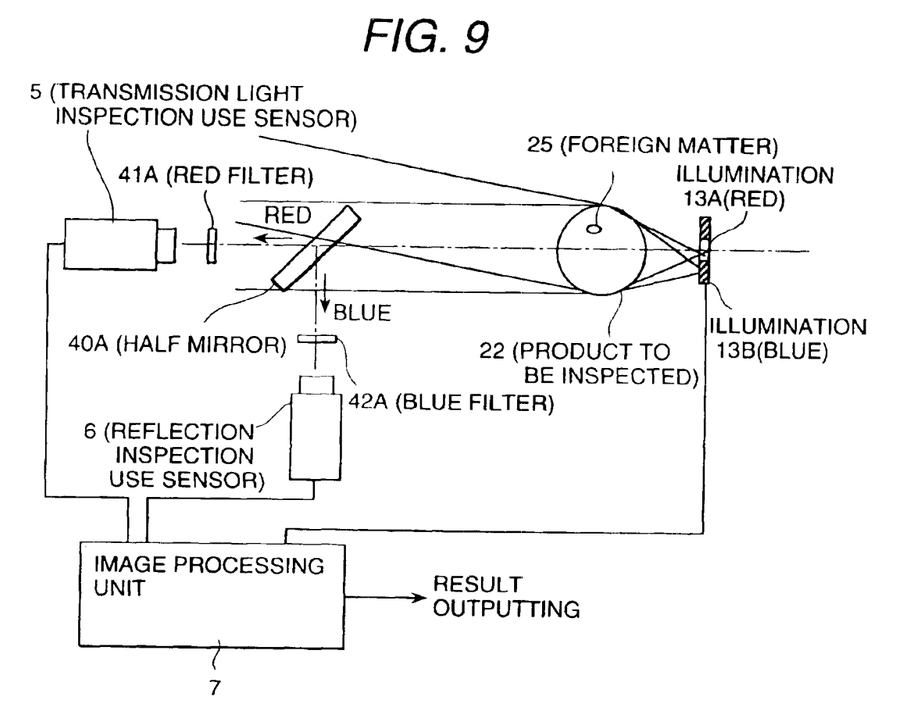
FIG. 9 is a diagram showing a foreign matter inspection device for inspecting foreign matters in a liquid filled transparent container representing a fifth embodiment according to the present invention.

FIG. 9 is a fifth embodiment of the present invention and is a modification of FIG. 3 embodiment. In FIG. 9, 40A is a half mirror, 41A is a red filter and 42A is a blue filter.

A foreign matter inspection is usually performed on a specifically provided inspection line. On the inspection line at a plurality of different positions respective sensors (cameras) are disposed and the respective sensors are designed to image a product to be inspected which comes into the respective view fields. The imaging is frequently performed in such a manner that before taking images of the product to be inspected the product is rotated and is suddenly stopped to only rotate the liquid therein and the images of the rotating liquid are taken. Since products to be inspected are successively delivered onto the inspection line, the respective sensors are required to perform high speed imaging. For the high speed imaging, the simultaneous irradiation of the illuminations 23A and 23B as well as simultaneous imaging are preferable. FIGS. 8 and 9 embodiments are such examples.

Figure 10:
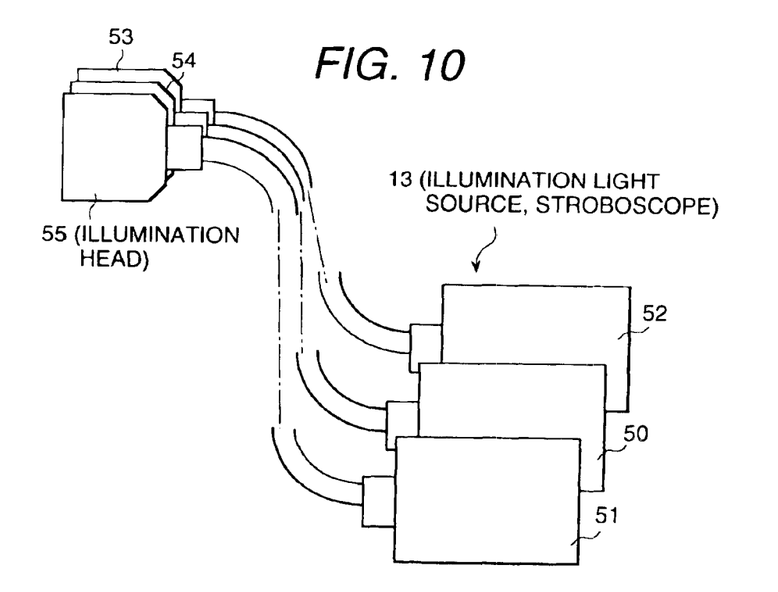
FIG. 10 is an outlook diagram showing another optical guide device which is applicable to the third through fifth embodiments as shown in FIGS. 4, 8 and 9.

In contrast to FIGS. 5(a) through 5(c) light guide device in which a single light source is used, FIG. 10 shows a light guide device including three light sources 50, 51 and 52. For the respective light sources 50, 51 and 52 corresponding illumination heads 54, 55 and 53 are provided. In the single light source as shown in FIGS. 5(a) through 5(b), the light is emitted at the same time from the three light emitting faces, however, with the three light sources, the light emission can be controlled independently. Accordingly, a successive control of turning ON light source 50, then turning ON light sources 51 and 52 and repeating the same can be performed.

The image processing unit 7 takes in the picture images from the two cameras, and performs foreign matter detection by making use of predetermined threshold values for the respective picture images.

According to the third through fifth embodiments, since the first and second irradiation light sources are provided near the product to be inspected behind thereof, a possible foreign matter in the liquid filled in the transparent container can be detected at the same time or at slightly deviated timings by making use of the transmission light and the irregular reflection light and the characteristics of the detected foreign matters can also be specified.

In the above embodiments, in order to distinguishing over the transmission light from the reflection light, the illumination lights of different colors, in other words, lights having different wavelengths are used. However, as an alternative lights having different polarization planes such as longitudinal wave and transversal wave can be used. In such instance respective polarizing filters has to be provided, for example, in front of the respective illuminations 23A and 23B, and the color filters in front of the respective inspection use sensors are replaced by concerned polarization filter.

What is claimed is:

1. A foreign matter inspection device for inspecting foreign matters in a liquid filled transparent container comprising:

a first irradiation light source which is disposed behind the transparent container and irradiates a first irradiation light to the transparent container;

a second irradiation light source which is disposed adjacent to the first irradiation light source and irradiates a second irradiation light of a different color from that of the first irradiation light from a different direction from that of the first irradiation light to the transparent container;

a color separation mirror which is disposed on a transmission light optical path of the first irradiation light from the transparent container as well as on a reflection light optical path of the second irradiation light from the transparent container, and which causes to advance in straight optical path the transmission light of the first irradiation light and performs color separation of the reflection light of the second irradiation light and guides the same in another optical path than that of the transmission light;

a first imaging means which is disposed on the straight advancing optical path and images the transmission light of the first irradiation light;

a second imaging means which is disposed on the another optical path and images the reflection light of the second irradiation light; and an image processing means which image processes picture images taken by the first and second imaging means and detects foreign matters in the liquid filled container.

2. A foreign matter inspection device for inspecting foreign matters in a liquid filled transparent container comprising:

a first irradiation light source which is disposed behind the transparent container and irradiates a first irradiation light to the transparent container;

a second irradiation light source which is disposed adjacent to the first irradiation light source and irradiates a second irradiation light of a different color from that of the first irradiation light from a different direction from that of the first irradiation light to the transparent container;

a half mirror which is disposed on a transmission light optical path of the first irradiation light from the transparent container as well as on a reflection light optical path of the second irradiation light from the transparent container and performs optical path separation;

a first filter which is disposed on a straight advancing optical path of the half mirror and selects the transmission light from the first irradiation light;

a first imaging means which images the transmission light of the first irradiation light selected by the first filter;

a second filter which is disposed on another optical path of the half mirror and selects the reflection light of the second irradiation light;

a second imaging means which images the reflection light of the second irradiation light selected by the second filter; and an image processing means which image processes picture images taken by the first and second imaging means and detects foreign matters in the liquid filled container.

3. A foreign matter inspection device for inspecting foreign matters in a liquid filled transparent container according to claim 2, wherein the first and second irradiation lights from the first and second irradiation light sources are guided through a light guide device.

* * * * *